US010942189B2

(12) United States Patent
Salamonsen et al.

(10) Patent No.: US 10,942,189 B2
(45) Date of Patent: Mar. 9, 2021

(54) PROGNOSTIC ASSAY FOR SUCCESS OF ASSISTED REPRODUCTIVE TECHNOLOGY

(71) Applicant: Prince Henry's Institute of Medical Research, Clayton (AU)

(72) Inventors: Lois Salamonsen, Kew (AU); Tracey Edgell, Blind Bight (AU); Natalie Hannan, Balwyn (AU); Luk Rombauts, Glen Iris (AU)

(73) Assignee: Hudson Institute of Medical Research, Clayton (AU)

( * ) Notice: Subject to any disclaimer, the term of this patent is extended or adjusted under 35 U.S.C. 154(b) by 5 days.

(21) Appl. No.: 15/301,521

(22) PCT Filed: Apr. 1, 2015

(86) PCT No.: PCT/AU2015/050147
§ 371 (c)(1),
(2) Date: Oct. 3, 2016

(87) PCT Pub. No.: WO2015/149129
PCT Pub. Date: Oct. 8, 2015

(65) Prior Publication Data
US 2017/0115302 A1 Apr. 27, 2017

(30) Foreign Application Priority Data
Apr. 2, 2014 (AU) .............................. 2014901190

(51) Int. Cl.
*C12Q 1/6883* (2018.01)
*G01N 33/68* (2006.01)

(52) U.S. Cl.
CPC ......... *G01N 33/689* (2013.01); *C12Q 1/6883* (2013.01); *C12Q 2600/118* (2013.01); *C12Q 2600/158* (2013.01); *G01N 2333/49* (2013.01); *G01N 2333/52* (2013.01); *G01N 2333/535* (2013.01); *G01N 2333/5421* (2013.01); *G01N 2800/368* (2013.01)

(58) Field of Classification Search
CPC .................................................. G01N 33/689
See application file for complete search history.

(56) References Cited

U.S. PATENT DOCUMENTS

2011/0104121 A1* 5/2011 Wira ..................... A61K 31/138
424/93.2

FOREIGN PATENT DOCUMENTS

WO 2007/130673 A2 11/2007
WO 2008/009705 A1 1/2008

OTHER PUBLICATIONS

Groeneveld, E., et al., 'Blood-borne angiogenic factors and sustained multiple implantation: a comparison of singleton and twin pregnancies', 2010, Reproductive BioMedicine Online, 2010, vol. 20, pp. 822-830.
Lédée, N., et al., 'Impact of follicular G-CSF quantification on subsequent embryo transfer decisions: a proof of concept study', Human Reproduction, 2013, vol. 28, pp. 406-413.
Rajaei, S., 'Cytokine profile in the endometrium of normal fertile and women with repeated implantation failure', Iranian Journal of Immunology, 2011, vol. 8, pp. 201-208.
Seo, W S., et al., 'Expression of endometrial protein markers in infertile women and the association with subsequent in vitro fertilization outcome', Fertility and Sterility, 2011, vol. 95, pp. 2707-2710.
Mang, P.-G., et al., 'Preliminary exploration of cytokines profiling in endometrial secretions and pregnancy outcomes during window of peri-implantation in ovarian stimulation cycles', Shengzhi Yu Biyun (Reproduction & Contraception), 2013, vol. 33, pp. 154-158 (Enlgish language Abstract).
Alhilali, Miaad Jabbar Sahib, et al., "IL-5 in follicular fluid as a negative predictor of the intracytoplasmic sperm injection outcome," Cytokine 113 (2019) 265-271.
Basuino, Lais, et al,"Human follicular fluid and effects on reproduction," JBRA Assisted Reproduction 2016;20 (1):38-40; doi: 10.5935/1518-0557.20160009.
Berlanga, O.,et al.,"How endometrial secretomics can help in predicting implantation," Placenta 32 (2011) S271-S275, Elsevier Ltd.
Hashish, N.M. et al., "Does flushing the endometrial cavity with follicular fluid after oocyte retrieval affect pregnancy rates in subfertile women undergoing intracytoplasmic sperm injection? A randomized controlled trial," European Journal of Obstetrics & Gynecology and Reproductive Biology 176 (2014) 153-157.
Macklon, Nick S., et al.,"The Science behind 25 Years of Ovarian Stimulation for in Vitro Fertilization," Endocrine Reviews 27(2):170-207 (2006) The Endocrine Society; doi: 10.1210/er.2005-0015.
Roque, Matheus, et al,"Freeze-all cycle in reproductive medicine: current perspectives," JBRA Assisted Reproduction 2017;21(1):49-53; doi: 10.5935/1518-0557.20170012.
Salamonsen, Lois, et al.,"Proteomics of the human endometrium and uterine fluid: a pathway to biomarker discovery," The Endometrium, Mar. 15, 2013, pp. 1087-1092, vol. 99, No. 4.
Strowitzki, Thomas, et al."The human endometrium as a fertility-determining factor," Human Reproduction Update, vol. 12, No. 5 pp. 617-630, 2006, Advance Access publication Jul. 10, 2006; doi:10.1093/humupd/dml033.

* cited by examiner

*Primary Examiner* — Yong S. Chong
(74) *Attorney, Agent, or Firm* — Banner & Witcoff, Ltd.

(57) ABSTRACT

The present disclosure teaches an assay to determine the likelihood of a successful implantation of an embryo into a female subject leading to a pregnancy. Enabled herein is an improved assisted reproduction technology protocol based on a prognostic evaluation of pregnancy outcomes. Taught herein is a composition comprising reagents required for the prognostic evaluation. Taught herein are assays comprising determination of levels of the biomarkers IL-8, G-CSF and/or VEGFA in a biological fluid sample taken before embryo implantation.

13 Claims, 5 Drawing Sheets ns PROGNOSTIC ASSAY FOR SUCCESS OF
ASSISTED REPRODUCTIVE TECHNOLOGY

RELATED APPLICATIONS

This application is a National Stage Application under 35 U.S.C. 371 of co-pending PCT application PCT/AU2015/050147 designating the United States and filed Apr. 1, 2015; which claims the benefit of AU application number 2014901190 and filed Apr. 2, 2014 each of which are hereby incorporated by reference in their entireties.

BACKGROUND

Field

The present disclosure teaches an assay to determine the likelihood of a successful implantation of an embryo into a female subject leading to a pregnancy. Enabled herein is an improved assisted reproduction technology protocol based on a prognostic evaluation of pregnancy outcomes. Taught herein is a composition comprising reagents required for the prognostic evaluation.

Description of Related Art

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Assisted reproductive technology (ART) has had a major impact on the ability for human females to achieve pregnancy with a successful outcome.

However, the ART process can be an emotional and stressful experience on recipients. The ability to reduce unsuccessful implantation outcomes would assist in reducing this stress and reducing overall costs of the procedure.

As an indicator of the prevalence of ART in the human clinical setting, a report by Macaldowie et al. (2013) *Assisted reproductive technology in Australia and New Zealand* 2011, Sydney: National Perinatal Epidemiology and Statistics Unit, the University of New South Wales, Australia, indicates that there was an 8.3% increase in Australian women undertaking this procedure in 2011. In 95.1% of cases, women used their own (autologous) oocytes or embryos. Approximately one third of women used frozen/thawed embryos. Despite this increase in the use of assisted reproductive technology, rates of successful clinical pregnancies are not overly high. In fact, in 2011, only 23.1% resulted in clinical pregnancy and 17.5% in live births (Macaldowie et al. (2013) supra).

A range of parameters, such as, age of the recipient, autologous and oocyte/embryo recipient cycles and use of fresh compared to frozen/thawed embryos has been investigated on their impact on the success or otherwise of ART. However, there is still a need for a knowledge-based assessment protocol to assist a clinician to determine whether the uterus of a female recipient is optimally prepared for embryo receptivity.

SUMMARY

The present specification teaches an improved protocol for assisted reproduction technology wherein at 2 days post ovulation induction trigger (OI+2 days) such as human chorionic gonadotropin trigger (hCG+2 days), gonadotropin releasing hormone analog trigger (GnRHa+2 days) or another drug rigger plus 2 days or early secretory phase equivalent, a biological fluid sample is taken to assess the receptivity of the endometrium. The biological sample includes a uterine sample or a blood, plasma, serum, ascites, lymph fluid, tissue exudate or urine sample. Particular biomarkers determine the degree of likelihood of a successful implantation of a fertilized embryo in that cycle and further whether a pregnancy is likely to be a clinical or preclinical pregnancy. The improved protocol enables a clinician to decide whether or not to proceed with embryo transfer or to freeze and store the embryo for subsequent use. Notwithstanding, the protocol can also be used to test endometrial receptivity in an assisted reproductive technology protocol. A composition is encompassed herein comprising reagents required to perform the protocol.

The present specification teaches, therefore, an endometrial receptivity test performed prior to the time window for implantation (i.e. at OI+5 days, e.g. hCG+5 days or GnRHa+5 days or mid-secretory phase equivalent). The assay developed in accordance with the present invention is able to be completed and the results interpreted in a timely manner to minimize interference in the uterine cavity at the time of embryo transfer/implantation. This reduces stress on a potential recipient, is efficient and has a high level of predictive outcome. The assay is knowledge-based in the context of a comparison of levels of biomarkers or ratios of levels of 2 or more biomarkers relative to control levels or ratios. Hence, provided herein is a knowledge-based assessment protocol which enables a clinician to determine the relative likelihood that an embryo transfer will lead to a successful clinical pregnancy.

The assay herein enables determination of predicted receptivity in a female subject during either a stimulated or natural cycle to ascertain whether a viable receptive endometrium will be present at the time of embryo transfer. This aids the clinician in determining whether to proceed with embryo transfer or to freeze embryos and wait for a natural cycle or alternatively another treated cycle in which uterine conditions are more favorable for a successful embryo transfer and implantation. The protocol can also be used to assess endometrial receptivity prior to hormonal stimulation.

In an embodiment, the sample is a uterine sample in the form of a uterine lavage sample obtained at the time of egg collection (two days after ovulation induction by hCG [hCG+2 days], GnRHa (GnRHa+2 days) or another drug (OI+2 days) in hormone stimulated cycles (or early secretory phase equivalent). Alternatively, the sample is blood, plasma or serum, ascites, lymph fluid, tissue exudate or urine. The biomarkers examined comprise IL-8, G-CSF and VEGFA. Additional markers contemplated herein include CRP, IL-17, IL-6 and progesterone. The assay determines favorable endometrial receptivity when one or more of IL-8 and/or G-CSF levels are low and/or VEGFA levels are high. Furthermore, levels of VEGFA are also useful in discriminating a recipient who will successfully develop clinical pregnancy compared to preclinical pregnancy. High VEGFA levels equate to a likelihood of a clinical pregnancy. A comparison of levels can be made to those who do become pregnant versus those who do not become pregnant.

Hence, enabled herein is an assay for stratifying a female subject with respect to likely outcome of embryo implantation, the outcome selected from pregnancy and no pregnancy, the assay comprising, determining the concentrations of biomarkers from a fluid sample from the subject, the biomarkers comprising IL-8, G-CSF and VEGFA, wherein the level or ratio of levels of the biomarkers provides an indication of the likelihood of a successful pregnancy. Additional markers may also be included selected from CRP, IL-17, IL-6 and progesterone.

Enabled herein is an assay for stratifying a female subject with respect to likely outcome of embryo implantation, the outcome selected from pregnancy and no pregnancy, the assay comprising, determining the concentrations of biomarkers from a uterine lavage sample from the subject, the biomarkers comprising IL-8, G-CSF and VEGFA, wherein the level or ratio of levels of the biomarkers provides an indication of the likelihood of a successful pregnancy. Additional markers may also be included selected from CRP, IL-17, IL-6 and progesterone.

Enabled herein is an assay for stratifying a female subject with respect to likely outcome of embryo implantation, the outcome selected from pregnancy and no pregnancy, the assay comprising, determining the concentrations of biomarkers from a blood, plasma or serum sample from the subject, the biomarkers comprising IL-8, G-CSF and VEGFA, wherein the level or ratio of levels of the biomarkers provides an indication of the likelihood of a successful pregnancy. Additional markers may also be included selected from CRP, IL-17, IL-6 and progesterone.

Further enabled herein is a multiplex assay to stratify a female subject undergoing an assisted reproductive technology protocol with respect to the likelihood of pregnancy or no pregnancy and if pregnant, whether the pregnancy is a clinical or preclinical pregnancy, the assay comprising determining the levels of biomarkers comprising IL-8, G-CSF and VEGFA in a fluid sample from the subject, wherein a successful pregnancy is considered likely when levels of IL-8 and/or G-CSF are low; a successful pregnancy is considered less likely when levels of IL-8 and/or G-CSF are high; a successful pregnancy is considered more likely if levels of VEGFA are high; a successful pregnancy is considered less likely if levels of VEGFA are low; a clinical pregnancy is considered a likely outcome if levels of VEGFA are high; a preclinical pregnancy is considered more likely if levels of VEGFA are low. A multivariate analysis may include biomarkers from more than one source (e.g. uterine lavage and serum) or biomarkers with body mass index (BMI) and age.

Taught herein is a kit to undertake an assay to determine levels of the one, two or all three biomarkers. A computer program is also contemplated herein to assist in the analysis of data. In an embodiment, the assay enabled herein may be used in existing knowledge-based architecture or platforms associated with pathology services. For example, results of the assays are transmitted via communications network (e.g. the internet) to a processing system in which an algorithm is stored and used to generate a predicted posterior probability value which translates to an index of likelihood of endometrial receptivity or non-receptivity leading to a successful pregnancy which is then forwarded to the clinician in the form of a prognostic or predictive report.

Taught herein, therefore, is a composition or kit or computer-based system which comprises reagents necessary to detect the concentration of biomarkers and the computer hardware and/or software to facilitate determination and transmission of reports to the clinician. Reference to "levels" of the biomarkers also encompasses determination of ratios of 2 or more of IL-8, G-CSF and/or VEGFA.

Whilst IL-8, G-CSF and VEGFA are the selected biomarkers, it is within the present invention to include additional biomarkers which may, for example, increase specificity and sensitivity. Additional markers include CRP, IL-17, IL-6 and progesterone. These may also be subject to multivariate analysis using patient physical parameters such as BMI and age.

Furthermore, the subject assay may be conducted prior to any stimulation in an assisted reproduction technology protocol to assess endometrial receptivity. The assay can also assist in predicting miscarriage.

The outcomes of the biomarker assays also enable the development of medicaments to facilitate endometrial receptivity and to assist in a more favorable outcome of clinical pregnancy. For example, IL-8 antagonists, G-CSF antagonists and VEGFA or VEGFA agonists are proposed to be useful in facilitating a successful embryo transfer outcome to a state of clinical pregnancy.

A list of abbreviations is provided in Table 1.

TABLE 1

Abbreviations

| Abbreviation | Definition |
|---|---|
| +2 | +2 days |
| +5 | +5 days |
| ART | Assisted reproduction technology |
| AUC | Area under the curve |
| BMI | Body mass index |
| CRP | C-reactive protein |
| CSF3 | Colony stimulation factor 3 (G-CSF) |
| G-CSF | Granulocyte-colony stimulating factor also known as CSF3 or colony stimulating factor 3 |
| GnRHa | Gonadotropin releasing hormone analog |
| GnRHa + 2 | Early secretory phase equivalent in a cycle in which GnRHa (or another stimulus) is used to trigger ovulation |
| GnRHa + 5 | Mid secretory phase equivalent in a cycle in which GnRHa (or another stimulus) is used to trigger ovulation |
| hCG | Human chorionic gonadotropin |
| hCG + 2 | Early secretory phase equivalent in a cycle in which hCG (or another stimulus) is used to trigger ovulation |
| hCG + 5 | Mid secretory phase equivalent in a cycle in which hCG (or another stimulus) is used to trigger ovulation |
| IL-6 | Interleukin-6 |
| IL-8 | Interleukin-8 |
| IL-17 | Interleukin-17 |
| IVF | In vitro fertilization |
| OI | Ovulation induction |
| OI + 2 | Early secretory phase equivalent in a cycle in which a drug is used to stimulate ovulation |
| OI + 5 | Mid secretory phase equivalent in a cycle in which a drug is used to stimulate ovulation |
| ROC | Receiver operating characteristics |
| VEGFA | Vascular endothelial growth factor |

DETAILED DESCRIPTION

Figure 1:
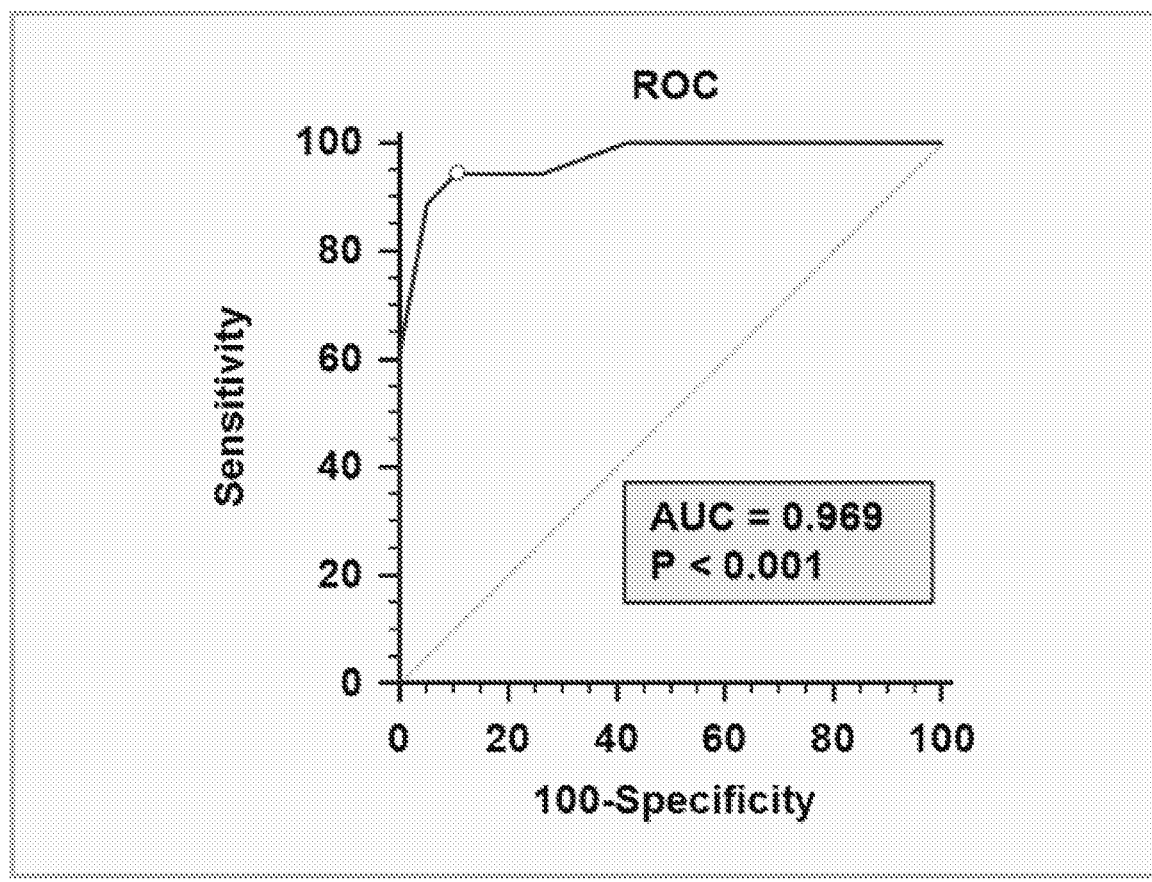
FIG. 1 is a graphical representation of an ROC plot of a multivariate algorithm combining G-CSF, IL-8 and VEGFA as a predictive indicator of idiopathic primary infertility. 91.9% of women were correctly classified.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a biomarker" includes a single biomarker, as well as two or more biomarkers; reference to "an embryo" includes a single embryo, as well as two or more embryos; reference to "the disclosure" includes single and multiple aspects taught by the disclosure; and so forth. Aspects taught and enabled herein are encompassed by the term "invention". All such aspects are enabled within the width of the present invention. Reference to a "sample" includes a uterine sample, or a sample of blood, plasma or serum, ascites, lymph fluid, tissue exudate or urine fluid.

The use of numerical values in the various ranges specified in this specification, unless expressly indicated otherwise, are stated as approximations as though the minimum and maximum values within the states ranges were both preceded by the word "about". Furthermore, the manner of collection, the volume of fluid and level of concentration (e.g. in lavage fluid versus aspirate) will result in different ranges. Notwithstanding, the skilled person would compensate for the "low" and "high" values given here for a particular range, without departing from the scope of the present invention. Also, the disclosure of these ranges is intended as a continuous range including every value between the minimum and maximum values. In addition, the subject protocol extends to ratios of two or more markers providing a numerical value associated with a level of likelihood of a successful embryo transfer leading to a clinical pregnancy. In terms of the values provided, these are based on a Luminex platform using milliplex kits. The use of a different assay platform may result in different values. A conversion factor can be applied to equate values for a different assay platform to a Luminex platform. A dilution factor for lavage is determined using the estimation: dilution factor=serum concentration divided by lavage urea concentration. Reference to "OI+2" means two days post ovulation induction by human chorionic gonadotropin (hCG) or by another drug or hormone such as but not limited to gonadotropin releasing hormone analog (GnRHa).

Reference to "success" in relation to a pregnancy does not necessary imply that the pregnancy will go to term. Other post implantation factors may result in miscarriage. Reference to a successful pregnancy means progression to a clinical pregnancy regardless of the ultimate result of the pregnancy.

A rapid, efficient and sensitive assay of endometrial receptivity is provided for the identification of human female subjects in whom an outcome of a successful pregnancy is likely following assisted reproductive technology.

The present disclosure teaches an assay to stratify potential human female recipients for autologous, frozen/thawed or heterologous embryo implantation in terms of likelihood or otherwise for a successful pregnancy. As indicated above, a successful pregnancy means progression to a clinical pregnancy. In essence, cytokine biomarkers are determined from a fluid sample which discriminate patients on likelihood of a pregnancy or no pregnancy and preclinical pregnancy or clinical pregnancy in the cycle of sampling and transfer. The biomarkers are also useful for determining the success or otherwise of a recipient achieving pregnancy using a donated egg or a donated fertilized embryo. The biomarkers may be considered as a panel alone or in combination with patient physical characteristics such as BMI and age. Reference to a "fluid sample" includes uterine lavage, blood, plasma and serum, ascites, lymph fluid, tissue exudate and urine. Biomarkers may be determined in a fluid sample from one source or from two or more sources (e.g. uterine lavage and serum).

The biomarkers comprise IL-8, VEGFA and G-CSF. This order of listed biomarkers is not intended to imply a weighting as to their importance or relevance to a prognostic outcome. Furthermore, additional biomarkers may be included such as CRP, IL-17, IL-6 and progesterone. The levels of these biomarkers, including ratios of levels of two or more biomarkers, are determined relative to a control. A control includes levels in a cohort of subjects under study or may be a statistically determined knowledge database obtained over a large number of studies. Reference is made to a "first knowledge base" which comprises data in the form of correlations between levels or ratios of levels of biomarkers and certain pregnancy outcomes. A second knowledge base represents data from a recipient undergoing the prognostic assay. Data in the second knowledge base are compared to the first knowledge base for a determination of the likelihood or otherwise of a successful pregnancy. In addition, biomarkers may be subject to multivariate analysis with physical parameters such as BMI and age as well as from two different sources (e.g. IL-8, G-CSF and VEGFA from uterine lavage and IL-6 and/or progesterone from blood, plasma or serum).

In essence, a human female subject may present for egg collection following a natural cycle or after hormone stimulated therapy. The levels or ratios of biomarkers measured at this time are useful for determining whether to proceed following fertilization of an embryo or to wait for another cycle. In an embodiment, an elevated level of IL-8 or G-CSF or a low level for VEGFA during this cycling phase are indicators of a poor likelihood of a successful pregnancy. Alternatively, low levels of IL-8 or G-CSF or high levels of VEGFA are indicators for a greater likelihood of a successful pregnancy. The assay results also apply to endometrial receptivity prior to hormonal stimulation in an assisted reproduction technology protocol and such an assay is contemplated herein.

At the time of egg collection the female subject is generally sedated and this is a convenient time to obtain a uterine sample to test levels of the biomarkers. In an embodiment, a soft catheter is used to infuse 1-10 ml of saline which is then recovered as uterine lavage. Whilst an aspirate sample is also suitable, for the purposes of the present protocol, a uterine lavage is considered optimal. Reference to "1-10 ml" of saline includes 1, 2, 3, 4, 5, 6, 7, 8, 9 and 10 ml. A range of 1-3 ml saline is considered optimal. The sample may be tested for protein levels or levels of corresponding mRNA which encodes for IL-8, G-CSF or VEGFA. Aspirates may be in the 5-1,000 µl range. In another embodiment, the biomarkers are determined from blood, plasma or serum, ascites, lymph fluid, tissue exudate or urine. In another embodiment, IL-8, G-CSF and VEGFA are determined in one sample (e.g. uterine lavage) and CRP, IL-17, IL-6 and/or progesterone is determined in another sample (e.g. blood, plasma or serum). In a further embodiment, IL-8, G-CSF, VEGFA, CRP, IL-17, IL-6 and progesterone are all determined alone or in combination with BMI and age.

Conveniently, at the time of sedation of the female subject and collection of the uterine sample, the levels and/or ratios of the biomarkers are determined to stratify the subject on expected outcome of embryo implantation. Outcomes include pregnancy or no pregnancy. For those subjects who achieve pregnancy, the biomarkers can also predict a clinical or preclinical pregnancy. In an embodiment, reduced levels of G-CSF is indicative of a likely outcome of pregnancy. Elevated G-CSF levels are indicative of a reduced likelihood of pregnancy. Similar results are obtained with IL-8. A reduced VEGFA level on the other hand is more likely to be associated with a poor pregnancy outcome. As indicated above, the assay can be used to assay endometrial receptivity prior to stimulation in an assisted reproduction technology protocol.

For those subjects achieving pregnancy, an elevated level of VEGFA is indicative of a likelihood of a clinical pregnancy compared to a preclinical pregnancy which is associated with reduced levels of VEGFA.

Hence, the present disclosure teaches a method for stratifying a human female subject with respect to expected outcomes of embryo implantation in an assisted reproduction technology protocol, the method comprising determining the levels of biomarkers in a fluid sample, the biomarkers comprising IL-8, G-CSF and/or VEGFA, wherein elevated levels of IL-8 and/or G-CSF are indicative of a low likelihood of a successful pregnancy and reduced levels of IL-8 and/or G-CSF are indicative of a high likelihood of a successful pregnancy and where reduced VEGFA levels is indicative of poor successful pregnancy outcome and, should pregnancy be achieved, that the pregnancy is preclinical rather than a clinical pregnancy.

Hence, elevated VEGFA levels are suggestive of a successful pregnancy and that the pregnancy is a clinical pregnancy. Additional markers or factors may also be determined including levels of CRP, IL-17 and/or IL-6 and the level of BMI and the patient's age.

Contemplated herein is an assay for stratifying a female subject with respect to likely outcome of embryo implantation, the outcome selected from pregnancy and no pregnancy, the assay comprising, determining the concentrations of biomarkers from a uterine sample from the subject selected from biomarkers comprising IL-8, G-CSF and VEGFA wherein the level or ratio of levels of the biomarkers provides an indication of the likelihood of a successful pregnancy.

Enabled herein is a multiplex assay to stratify a female subject undergoing an assisted reproductive technology protocol with respect to the likelihood of pregnancy or no pregnancy and if pregnant, whether the pregnancy is a clinical or preclinical pregnancy, the assay comprising determining the levels of IL-8, G-CSF and VEGFA in a fluid from the subject, wherein a successful pregnancy is considered likely when levels of IL-8 and/or G-CSF are low; a successful pregnancy is considered less likely when levels of IL-8 and/or G-CSF are high; a successful pregnancy is considered more likely if levels of VEGFA are high; a successful pregnancy is considered less likely if levels of VEGFA are low; a clinical pregnancy is considered a likely outcome if levels of VEGFA are high; a preclinical pregnancy is considered more likely if levels of VEGFA are low.

In an embodiment, the fluid sample is a uterine lavage sample. In another embodiment, the fluid sample is blood, plasma, serum, ascites, lymph fluid, tissue exudate or urine.

In an embodiment, the female recipient is either undergoing hormone assisted cycle or is naturally cycling. In an embodiment, endometrial receptivity is assessed prior to initiation of any hormonal assisted cycling.

Whilst it is most convenient for the uterine sample to be taken once during egg collection, the present protocol does not preclude multiple samples being obtained. However, optimally, the female subject is sampled once at the time of egg collection or, for female subjects having a frozen/thawed embryo, the sample is conducted at OI+2 (e.g. hCG+2 or GnRH+2 or OI trigger by another drug)) days for hormonal assisted cycles or at an early secretory phase equivalent. Ovulation induction may be by hCG or another drug such as but not limited to GnRHa. Blood or other fluid sample may be taken at any time and is far less invasive. Conveniently, non-lavage samples are taken at the same time that the patient presents for egg collection.

The levels or ratios of levels of the biomarkers may be compared to the same subject as she undergoes cycling or is in a non-cycling phase or may be compared to a cohort of females undergoing a similar procedure or may be compared to a first knowledge database collected over a statistical number of trials. As indicated above, the levels of biomarkers determined in a test subject represent a second knowledge base of unknown predictive outcomes. The second knowledge base is compared to the first knowledge base.

Whilst not intending to limit the interpretation of the subject method to particular values of "elevated" or "reduced" levels of biomarkers, an example of reduced versus elevated G-CSF is 0-2,000 picograms/ml sample for reduced and 3,000 to 10,000 picograms/ml sample for elevated. These numbers are representative from a 3 ml uterine lavage and will alter depending on the precise method of sample collection.

An example of reduced levels of VEGFA is from 0 to 20 picograms/ml of sample and elevated levels are 30 to 100 picograms/ml sample. These numbers are representative from a 3 ml uterine lavage and will alter depending on the precise method of sample collection.

An example of reduced IL-8 is 0-15 picograms/ml sample and elevated IL-8 is 20 to 100 picograms/ml sample. These numbers are representative from a 3 ml uterine lavage and will alter depending on the precise method of sample collection.

Those are based on a Luminex platform. Ranges may differ based on the pathology platform used.

The present invention is not to be limited to these ranges across all female subjects but the ranges given here provide a guide only as to likely levels which will be monitored by a clinician. In addition, physical characteristics of the patient may be considered such as BMI and age.

In particular, the stratification assay enabled herein may be used in existing knowledge-based architecture or platforms associated with pathology/clinical services. In an embodiment, the results from the assays are transmitted via a communications network (e.g. the internet) to a processing system in which an algorithm is stored and used to generate a predicted posterior probability value which translates to a probability of a particular outcome which is then forwarded to an end user (e.g. clinician) in the form of a prognostic or predictive report.

The assay may, therefore, be in the form of a kit or computer-based system which comprises the reagents necessary to detect the concentration of the biomarkers and the computer hardware and/or software facilitates determination and transmission of reports to a clinician.

Hence, enabled herein is a cohort of biomarkers comprising IL-8, G-CSF and/or VEGFA. This cohort includes a panel of biomarker-binding agents or ligands which is used to determine the levels any one of the biomarkers, two or more of the biomarkers or all three of the biomarkers. Hence, the uterine or other sample may be tested for biomarkers comprising IL-8, G-CSF, VEGFA, IL-8+G-CSF, IL-8+VEGFA, G-CSF+VEGFA, IL-8+VEGFA or IL-8+G-CSF+VEGFA. Ratios of two or more of IL-8, G-CSF and/or VEGFA may also be determined. These biomarkers may also be tested prior to initiation of any hormonal therapy to assess endometrial receptivity. Additional biomarkers may be included such as CRP, IL-17, IL-6 and/or progesterone.

Enabled herein is a prognostic assay for stratifying a female subject with respect to likely outcomes of embryo implantation, the outcome selected from pregnancy and no pregnancy and if pregnant, a clinical pregnancy or preclinical pregnancy, the assay comprising determining the concentration of biomarkers in a fluid sample from the subject selected from IL-8, G-CSF and VEGFA; wherein the level or ratio of levels of the biomarkers provides an indication of the likelihood of a successful pregnancy. As indicated above, any one or more of the three biomarkers may be selected and assayed. Measuring all three is likely to increase the level of sensitivity and specificity of the prognostic assay result. Additional biomarkers may also be included without departing from the scope of the subject invention.

Further enabled herein is a prognostic assay for stratifying a female subject with respect to likely outcomes of embryo implantation, the outcome selected from pregnancy and no pregnancy and if pregnant, a clinical pregnancy or preclinical pregnancy, the assay comprising determining the concentration of biomarkers in a fluid sample from the subject selected from IL-8, G-CSF, VEGFA, CRP, IL-17, IL-6 and progesterone. As indicated above, any one or more of IL-8, G-C3F or G-CSF or two or more of IL-8, G-CSF, VEGFA, CRP, IL-17, IL-6 or progesterone. In addition, the "outcome" includes a miscarriage or a likelihood that the pregnancy will not go to term.

In an embodiment, the fluid sample is uterine lavage. In an embodiment, the fluid sample is blood, plasma, serum, ascites, lymph fluid, tissue exudate or urine. In an embodiment, the biomarkers are determined in two or more different fluid samples.

In an embodiment, taught herein is an assay for stratifying a female subject with respect to likely outcome of embryo implantation, the assay comprising determining the concentration of biomarkers in a fluid sample from the subject selected from biomarkers comprising IL-8, G-CSF and VEGFA; subjecting the levels to an algorithm generated from a first knowledge base of data comprising the levels of the same biomarkers from subjects of known status with respect to the outcome wherein the algorithm provides an index of probability of the subject proceeding or not proceeding with a pregnancy. Reference to the "algorithm" is an algorithm which performs a multivariate analysis function. The latter may include factors such as BMI and age. The algorithm may further distinguish between clinical and preclinical pregnancy.

In an embodiment, the female subject is undergoing hormone stimulation. In an alternative embodiment, the female subject is experiencing a natural ovulation cycle.

The first knowledge base of data may also come from multiple subjects or cohorts of subjects with known outcome of pregnancy.

The determination of the concentrations or levels of the biomarkers enables establishment of a diagnostic rule based on the concentrations of biomarkers relative to controls. Alternatively, the diagnostic rule is based on the application of a statistical and machine learning algorithm. Such an algorithm uses relationships between biomarkers and implantation outcome observed in training data (with known outcome status) to infer relationships which are then used to predict the status of an implantation even with unknown status. An algorithm is employed which provides an index of probability that a subject will become pregnant and, once pregnant, the likely status of the pregnancy in terms of a clinical pregnancy or preclinical pregnancy. The algorithm performs a multivariate analysis function.

Hence in one embodiment, the present invention provides a diagnostic rule based on the application of statistical and machine learning algorithms. Such an algorithm uses the relationships between biomarkers and implantation outcome status observed in training data (with known implantation status) to infer relationships which are then used to predict the status of subjects with unknown status. Practitioners skilled in the art of data analysis recognize that many different forms of inferring relationships in the training data may be used without materially changing the present invention.

The present invention contemplates the use of a knowledge base of training data comprising levels of biomarkers from a subject with a known implantation outcome to generate an algorithm which, upon input of a second knowledge base of data comprising levels of the same biomarkers from a subject with an unknown implantation outcome likelihood, provides an index of probability that predicts the probable outcome.

The "subject" is generally a human female. In an embodiment, the human female is in a selected within child bearing age range. However, the present invention extends to veterinary applications. Hence, the subject may be a non-human female mammal such as a bovine, equine, ovine animal or a non-human primate. Notwithstanding, the present invention is particularly applicable to detecting the outcome of an embryo implantation event in a human female.

The term "training data" includes knowledge of levels of biomarkers relative to a control. This is the first knowledge base. A "control" includes levels of biomarkers in a subject or cohort of subjects of known implantation success or failure status or may be a statistically determined level based on trials. The term "levels" also encompasses ratios of levels of biomarkers.

The "training data" also include the concentration of one or more of IL-8, G-CSF and/or VEGFA. The data may comprise information on an increase or decrease in these biomarkers. Additional biomarkers may also be included such as CRP, IL-17, IL-6 and/or progesterone.

The present invention further contemplates a panel of agents for stratification of a female subject undergoing assisted reproduction, the panel comprising agents which bind specifically to biomarkers, the biomarkers comprising IL-8, G-CSF and/or VEGFA, which are used to determine levels of one or more of the biomarkers and then subjecting the levels to an algorithm generated from a first knowledge base of data comprising the levels of the same biomarkers from a subject of known status with respect to embryo implantation wherein the algorithm provides an index of probability of the subject having or not having a successful pregnancy. A "successful" pregnancy is one leading to a clinical pregnancy. Subsequent events leading to a miscarriage are not contemplated in the definition of a "successful"

pregnancy. Additional biomarkers such as CRP, IL-17, IL-6 and/or progesterone may be detected.

The levels or concentrations of the biomarkers in an assayed female subject provide the input test data referred to herein as a "second knowledge base of data". The second knowledge base of data either is considered relative to a control or is fed into an algorithm generated by a "first knowledge base of data" which comprise information of the levels of biomarkers in a subject with a known implantation outcome. The second knowledge base of data is from a subject or cohort of subjects of unknown status with respect to an embryo implantation event. The output of the algorithm is a probability or likelihood factor, referred to herein as an index of probability, of a subject having a successful pregnancy in terms of ultimately achieving a clinical pregnancy. Levels may be determined in one type of fluid sample (e.g. uterine lavage or serum) or from two or more sources (e.g. uterine lavage and serum).

The agents which "specifically bind" to the biomarkers generally include an immunointeractive molecule such as an antibody or hybrid, derivative including a recombinant or modified form thereof or an antigen-binding fragment thereof. The agents may also be a receptor or other ligand. These agents assist in determining the level of the biomarkers.

Hence, the present invention further provides a panel of immobilized ligands to a biomarker selected from IL-8, G-CSF and/or VEGFA. The panel may comprise ligands to 1, 2 or all 3 biomarkers. Additional biomarkers may also be included such as CRP, IL-17, IL-6 and/or progesterone. In an embodiment, the panel is a composition of reagents in the form of ligands to 1, 2 or all 3 biomarkers. Such ligands include antibodies to IL-8, G-CSF and/or VEGFA. A composition of reagents is also contemplated comprising binding or detecting agents for three or more of IL-8, G-CSF, VEGFA, CRP, IL-17, IL-6 and progesterone with the proviso that the binding or detecting reagents are at least specific for two or more of IL-8, G-CSF and/or VEGFA.

Still another aspect of the present invention contemplates a composition or kit for stratifying a female subject with respect to outcome of assisted reproduction, the kit comprising a composition of matter comprising one or more ligands to IL-8, G-CSF and/or VEGFA; the kit further comprising reagents to facilitate determination of the concentration of biomarker binding to a ligand. In use, the kit facilitates the determination of biomarkers. The levels or ratios of levels are then compared to a control or subjected to an algorithm generated from a first knowledge base of data comprising the levels of the same biomarkers from a subject or cohort of subjects of known status with respect to implantation outcome wherein the algorithm provides an index of probability of the subject having or not having the particular outcome. In an embodiment, the outcome is pregnancy or no pregnancy. In other embodiment the outcome is clinical pregnancy or preclinical pregnancy.

The ligands, such as antibodies specific to each of the biomarkers, enable the quantitative or qualitative detection or determination of the level of the at least two or more biomarkers. Reference to "level" includes concentration as weight per volume, activity per volume or units per volume or other convenient representative as well as ratios of levels.

The "sample" includes a uterine sample such as a uterine lavage or aspirate. A uterine lavage provides the most consistency of data. Notwithstanding, the assay may be modified to use blood, plasma or serum, ascites, lymph fluid, tissue exudate or urine. Alternatively, the sample is a tissue sample which is biochemically examined.

Identifying levels of at least IL-8, G-CSF and/or VEGFA in subjects undergoing an assisted reproduction technology protocol is useful in stratifying the outcome of the implantation. A person of ordinary skill in the art, based on the disclosure herein, can also identify additional biomarkers which may provide improved selectivity and sensitivity. Such an identification is still considered to be within the scope of the present invention.

As indicated above, the "ligand" or "binding agent" and like terms, refers to any compound, composition or molecule capable of specifically or substantially specifically (that is with limited cross-reactivity) binding to an epitope on the biomarker. The "binding agent" generally has a single specificity. Notwithstanding, binding agents having multiple specificities for two or more biomarkers are also contemplated herein. The binding agents (or ligands) are typically antibodies, such as monoclonal antibodies, or derivatives or analogs thereof, but also include, without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies; such as disulfide stabilized Fv fragments, scFv tandems [(scFv)$_2$ fragments], diabodies, tribodies or tetrabodies, which typically are covalently linked or otherwise stabilized (i.e. leucine zipper or helix stabilized) scFv fragments. "Binding agents" also include aptamers, as are described in the art.

Methods of making antigen-specific binding agents, including antibodies and their derivatives and analogs and aptamers, are well-known in the art. Polyclonal antibodies can be generated by immunization of an animal. Monoclonal antibodies can be prepared according to standard (hybridoma) methodology. Antibody derivatives and analogs, including humanized antibodies can be prepared recombinantly by isolating a DNA fragment from DNA encoding a monoclonal antibody and subcloning the appropriate V regions into an appropriate expression vector according to standard methods. Phage display and aptamer technology is described in the literature and permit in vitro clonal amplification of antigen-specific binding reagents with very affinity low cross-reactivity. Phage display reagents and systems are available commercially, and include the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Aptamer technology is described for example and without limitation in U.S. Pat. Nos. 5,270,163; 5,475,096; 5,840,867 and 6,544,776.

ECLIA, ELISA and Luminex LabMAP immunoassays are examples of suitable assays to detect levels of the biomarkers. In one example a first binding reagent/antibody is attached to a surface and a second binding reagent/antibody comprising a detectable group binds to the first antibody. Examples of detectable-groups include, for example and without limitation: fluorochromes, enzymes, epitopes for binding a second binding reagent (for example, when the second binding reagent/antibody is a mouse antibody, which is detected by a fluorescently-labeled anti-mouse antibody), for example an antigen or a member of a binding pair, such as biotin. The surface may be a planar surface, such as in the case of a typical grid-type array (for example, but without limitation, 96-well plates and planar microarrays) or a non-planar surface, as with coated bead array technologies, where each "species" of bead is labeled with, for example, a fluorochrome (such as the Luminex technology described in U.S. Pat. Nos. 6,599,331, 6,592,822 and 6,268,222), or quantum dot technology (for example, as described in U.S. Pat. No. 6,306,610). Such assays may also be regarded as laboratory information management systems (LIMS).

In the bead-type immunoassays, the Luminex LabMAP system can be utilized. The LabMAP system incorporates polystyrene microspheres that are dyed internally with two spectrally distinct fluorochromes. Using precise ratios of these fluorochromes, an array is created consisting of 100 different microsphere sets with specific spectral addresses. Each microsphere set can possess a different reactant on its surface. Because microsphere sets can be distinguished by their spectral addresses, they can be combined, allowing up to 100 different analytes to be measured simultaneously in a single reaction vessel. A third fluorochrome coupled to a reporter molecule quantifies the biomolecular interaction that has occurred at the microsphere surface. Microspheres are interrogated individually in a rapidly flowing fluid stream as they pass by two separate lasers in the Luminex analyzer. High-speed digital signal processing classifies the microsphere based on its spectral address and quantifies the reaction on the surface in a few seconds per sample.

As used herein, "immunoassay" refers to immune assays, typically, but not exclusively sandwich assays, capable of detecting and quantifying a desired biomarker, namely one or more of IL-8, G-CSF and/or VEGFA. Additional biomarkers may also be measured such as CRP, IL-17, IL-6 and/or progesterone.

Data generated from an assay to determine uterine (or other sample) levels of one or more of IL-8, G-CSF and/or VEGFA, can be used to determine the likelihood of progression of an embryo implantation event to clinical pregnancy in a female subject. The input of data comprising the levels of one or more biomarkers is compared with a control or is put into the algorithm which provides a likelihood value of a successful pregnancy. By "successful pregnancy" as indicated above, refers to a pregnancy. Further outcomes such as a clinical or preclinical pregnancy can also be discriminated. An assisted reproductive treatment regime can also be monitored by the subject prognostic assay.

As described above, methods are taught herein for stratifying a female subject for expected outcome of embryo implantation by determining levels of specific identified biomarkers and using these levels as second knowledge base data in an algorithm generated with first knowledge base data or levels of the same biomarkers in patents with a known implantation outcome. Also provided are methods of discriminating preclinical from clinical pregnancy comprising determining the presence and/or velocity of specific identified biomarkers selected from at least IL-8, G-CSF and VEGFA in a subject's fluid sample. By "velocity" it is meant the change in the concentration of the biomarker in a patient's sample over time.

The term "control sample" includes any sample that can be used to establish a first knowledge base of data from subjects with a known embryo implantation outcome.

The method of the subject invention may be used in the determination of the likely outcome of a cycle of assist reproductive technology (i.e. pregnancy or not pregnancy). The present invention may also be used to monitor the progression of a pregnancy and to monitor whether a particular treatment is effective or not pre-implantation. In particular, the method can be used to confirm the present or absence of conditions in the endometrium to be most receptive for implantation to occur and proceed to a clinical pregnancy.

As indicated above, antibodies may be used in any of a number of immunoassays which rely on the binding interaction between an antigenic determinant of the biomarker and the antibodies. Examples of such assays are radioimmunoassay, enzyme immunoassays (e.g. ECLIA, ELISA), immunofluorescence, immunoprecipitation, latex agglutination, hemagglutination and histochemical tests. The antibodies may be used to detect and quantify the level of the biomarker in a sample in order to determine endometrium receptivity leading to a level of likelihood of a successful pregnancy.

In particular, the antibodies of the present invention may also be used in immunohistochemical analyses, for example, at the cellular and subcellular level, to detect a biomarker, to localize it to particular cells and tissues, and to specific subcellular locations, and to quantitate the level of expression.

Cytochemical techniques known in the art for localizing antigens using light and electron microscopy may be used to detect the biomarker. Generally, an antibody of the present invention may be labeled with a detectable substance and a biomarker protein may be localized in tissues and cells based upon the presence of the detectable substance. Examples of detectable substances include, but are not limited to, the following: radioisotopes (e.g. $^{3}$H, $^{14}$C $^{35}$S, $^{125}$I, $^{131}$I), fluorescent labels (e.g. FITC, rhodamine, lanthanide phosphors), luminescent labels such as luminol; enzymatic labels (e.g. horseradish peroxidase, beta-galactosidase, luciferase, alkaline phosphatase, acetylcholinesterase), biotinyl groups (which can be detected by marked avidin e.g. streptavidin containing a fluorescent marker or enzymatic activity that can be detected by optical or calorimetric methods), predetermined polypeptide epitopes recognized by a secondary reporter (e.g leucine zipper pair sequences, binding sites for secondary antibodies, metal binding domains; epitope tags). In some embodiments, labels are attached via spacer arms of various lengths to reduce potential steric hindrance. Antibodies may also be coupled to electron dense substances, such as ferritin or colloidal gold, which are readily visualized by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip) Indirect methods may also be employed in which the primary antigen-antibody reaction is amplified by the introduction of a second antibody, having specificity for the antibody reactive against biomarker protein. By way of example, if the antibody having specificity against biomarker protein is a rabbit IgG antibody, the second antibody may be goat anti-rabbit gamma-globulin labeled with a detectable substance as described herein.

Where a radioactive label is used as a detectable substance, the biomarker may be localized by radioautography. The results of radioautography may be quantitated by determining the density of particles in the radioautographs by various optical methods.

The methods of the present invention described herein may also be performed using microarrays, such as oligonucleotide arrays, cDNA arrays, genomic DNA arrays, or antibody arrays.

In an embodiment, the method of the present invention involves the detection of mRNA encoding the biomarkers and to determine the level of biomarkers based on level of expression. Those skilled in the art can construct nucleotide probes for use in the detection of mRNA sequences encoding the biomarker(s) in samples. Suitable probes include nucleic acid molecules based on nucleic acid sequences encoding at least five sequential amino acids from regions of the biomarker, preferably they comprise 15 to 30 nucleotides. A nucleotide probe may be labeled with a detectable substance such as a radioactive label which provides for an adequate signal and has sufficient half-life such as $^{32}P$, $^{3}H$, $^{44}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, *Molecular Cloning, A Laboratory Manual*. (2nd ed.), 1989. The nucleic acid probes may be used to detect genes, that encode the biomarker(s). In an embodiment, the probes are used in the stratification of a female subject by specifically determining the level of expression of a biomarker.

The probe may be used in hybridization techniques to detect expression of genes that encode biomarker proteins. The technique generally involves contacting and incubating nucleic acids (e.g. mRNA) obtained from a uterine sample from female subject or other cellular source with a probe under conditions favorable for the specific annealing of the probes to complementary sequences in the nucleic acids. After incubation, the non-annealed nucleic acids are removed, and the presence of nucleic acids that have hybridized to the probe if any are detected.

The detection of mRNA may involve converting the mRNA to cDNA and/or the amplification of specific gene sequences using an amplification method such as polymerase chain reaction (PCR), followed by the analysis of the amplified molecules using techniques known to those skilled in the art. Suitable primers can be routinely designed by one of skill in the art.

Hybridization and amplification techniques described herein may be used to assay qualitative and quantitative aspects of expression of genes encoding the biomarker. For example, RNA may be isolated from a cell type or tissue known to express a gene encoding the biomarker, and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting symptoms of a cancer involving a biomarker protein or gene.

The primers and probes may be used in the above described methods in situ i.e. directly on tissue sections (fixed and/or frozen) of patient tissue obtained from uterine biopsies.

The present invention provides a method of stratifying a female subject with respect to the likelihood of a particular outcome of embryo implantation comprising:

(a) providing a fluid sample from the subject;
(b) extracting nucleic acid molecules comprising mRNA from a biomarker gene or portion thereof selected from IL-8, G-CSF and VEGFA from the sample;
(c) amplifying the extracted mRNA using the polymerase chain reaction;
(d) determining the level of mRNA encoding the biomarker; and
(e) subjecting the levels of one or more of the biomarkers to an algorithm which provides an index of probability of the likely outcome of embryo implantation. Additional markers may be determined such as CRP, IL-17, IL-6 and/or progesterone. A "fluid sample" includes in one embodiment, uterine lavage. In another embodiment, it is blood, plasma, serum, ascites, lymph fluid, tissue exudate or urine. In yet another embodiment, two or more fluid samples are screened for biomarkers. In an embodiment, biomarker levels are determined and subject to multivariate analysis in combination with BMI and/or age of the patient.

The methods described herein may be performed by utilizing pre-packaged diagnostic kits comprising the necessary reagents to perform any of the methods of the invention. For example, the kits may include at least one specific nucleic acid or antibody described herein, which may be conveniently used, e.g. in clinical settings, to screen and diagnose patients and to screen and identify those individuals with an endometrium receptive for successful implantation of an embryo. The kits may also include nucleic acid primers for amplifying nucleic, acids encoding the biomarker in the polymerase chain reaction. The kits can also include nucleotides, enzymes and buffers useful in the method of the invention as well as electrophoretic markers such as a 200 bp ladder. The kit also includes detailed instructions for carrying out the methods of the present invention.

Enabled herein is an algorithm-based screening assay to screen samples from female subjects undergoing an assisted reproduction technology protocol. Generally, input data are collected based on levels of one or more biomarkers (or levels of expression of genes encoding two or more biomarkers) selected from IL-8, G-CSF and VEGFA and subjected to an algorithm to assess the statistical significance of any elevation or reduction in levels which information is then output data. Computer software and hardware for assessing input data are encompassed by the present invention.

Another aspect of the present invention contemplates a method of treating a female subject undergoing an assisted reproduction technology protocol, the method comprising subjecting the subject to a diagnostic assay to determine the levels of one or more of IL-8, G-CSF and/or VEGFA to generate an index of probability of an embryo implantation being successful, and where there is a risk of the female subject having a non-receptive endometrium providing the subject an agonist or antagonist of the biomarkers to generate a receptive endometrium.

The present invention further provides the use the levels of one or more biomarkers selected from IL-8, G-CSF and VEGFA in the generation of an index of probability for use in a diagnostic assay to predict a particular outcome following embryo implantation.

The assay of the present invention permits integration into existing or newly developed pathology architecture or platform systems. For example, the present invention contemplates a method of allowing a user to determine the status of a subject with respect to a predicted outcome of embryo implantation, the method including:

(a) receiving data in the form of levels or concentrations of IL-8, G-CSF and/or VEGFA from the user via a communications network;

(b) processing the subject data via an algorithm which provides a likelihood index value;

(c) determining the status of the subject in accordance with the results of the likelihood index value in comparison with predetermined values; and (d) transferring an indication of the status of the subject to the user via the communications network.

Conveniently, the method generally further includes:

(a) having the user determine the data using a remote end station; and (b) transferring the data from the end station to the base station via the communications network.

The base station can include first and second processing systems, in which case the method can include:

(a) transferring the data to the first processing system;

(b) transferring the data to the second processing system; and (c) causing the first processing system to perform the algorithmic function to generate the likelihood index value.

The method may also include:

(a) transferring the results of the algorithmic function to the first processing system; and (b) causing the first processing system to determine the status of the subject.

As indicated above, other biomarkers may be screened such as CRP, IL-17, IL-6 and/or progesterone.

Reference to an "algorithm" or "algorithmic functions" as outlined above includes the performance of a multivariate analysis function. A range of different architectures and platforms may be implemented in addition to those described above. It will be appreciated that any form of architecture suitable for implementing the present invention may be used. However, one beneficial technique is the use of distributed architectures. In particular, a number of end stations may be provided at respective geographical locations. This can increase the efficiency of the system by reducing data bandwidth costs and requirements, as well as ensuring that if one base station becomes congested or a fault occurs, other end stations could take over. This also allows load sharing or the like, to ensure access to the system is available at all times.

In this case, it would be necessary to ensure that another base station contains the same information and signature such that different end stations can be used.

It will also be appreciated that in one example, the end stations can be hand-held devices, such as PDAs, mobile phones, or the like, which are capable of transferring the subject data to the base station via a communications network such as the Internet, and receiving the reports.

In the above aspects, the term "data" means the levels or concentrations of the biomarkers. The "communications network" includes the internet. When a server is used, it is generally a client server or more particularly a simple object application protocol (SOAP).

EXAMPLES

Aspects disclosed herein are further described by the following non-limiting Examples.

Example 1

Endometrial Receptivity Test

An endometrial receptivity predictive test is performed prior to the window of implantation (hCG+5 days or mid secretory phase equivalent) for use in an IVF clinic. hCG may be replaced by another drug (e.g. GnRHa) which is capable of inducing an ovulation induction trigger. This is both to permit time for the assay procedure to be completed and results reported/interpreted, and to minimize interference in the uterine cavity at the time of embryo transfer/implantation. Ten proposed endometrial receptivity markers (identified in receptive mid-secretory phase studies) are tested on a cohort of uterine lavage samples collected from fertile and infertile women. Unlike previous studies, these samples were collected during the early secretory (pre-receptive) phase of their natural cycle.

The cohort comprised fertile (n=19) and primary idiopathic infertile (n=18) women for whom male factor, ovulatory, and tubal defects having been eliminated as causative of their infertility. Inclusion criteria are provided in Table 2.

TABLE 2

Inclusion and exclusion criteria of women included in identification of early secretory markers of endometrial receptivity

|  | Fertile Women | Infertile Women |
| --- | --- | --- |
| Number | 19 | 18 |
| Age (mean +/− std. dev) | 36 +/− 4 years | 35 +/− 5 years |
| Inclusion Criteria | Prior natural pregnancy | No prior pregnancy |
| Exclusion Criteria | Ovarian or tubal pathology | Male factor, Ovarian or tubal pathology |

Kruskal-Wallis analysis of results for individual analytes and their ratios found statistically significant differences between fertile and infertile women for G-CSF (p=0.007), and the ratios of G-CSF/VEGFA (0.004) and VEGFA/IL-8 (0.078). Among the other analytes tested, no others provided statistically significant differentiation of fertile and infertile.

Receiver Operator Curve analysis (ROC) analysis found significant results for G-CSF (AUC=0.760, p=0.001). VEGFA and IL-8 while not achieving significance they did provide positive AUC values of 0.658 and 0.589, respectively. Ratios of the three analytes were also analysed by ROC curve, revealing significant results for G-CSF/VEGFA (AUC=0.778, p=0.001), and VEGFA/IL-8 (AUC=0.670, p=0.066).

Multivariate logistic analysis identified that a combination of G-CSF, VEGFA and IL-8 provided a diagnostic signature with a 91.9% diagnostic efficiency (AUC of ROC=0.969, p<0.001) as shown in FIG. 1. Data show a high level of sensitivity and specificity. Of the three women misclassified, two were fertile and one infertile. It should be noted that when assessing these data that current literature does not ascertain whether women are fertile every cycle or indeed if fertility is maintained, thus it may be that some women collected as previously fertile are no longer. With regards the infertile woman that was misclassified it is conceivable that her infertility is unrelated to any endometrial defect.

The study reported in this Example examined samples collected in natural cycles during the early secretory phase from women designated as having normal fertility or primary idiopathic infertility. The intended utility of this test, however, are women undergoing assisted reproductive technologies (ART) due to unexplained infertility where non-receptive endometrium may be suspected. These women are for the most part undergoing stimulated cycle. While it can be envisaged that testing of endometrial receptivity prior to initiating ART stimulation may be useful, it is perhaps more essential to predict receptivity in stimulated cycles to ascertain whether a viable receptive endometrium is present at the time of embryo transfer. This aids the clinician in determining whether to go ahead with embryo transfer or to freeze embryos and wait for a natural cycle or alternatively treated cycle in which uterine conditions may be more favorable to a successful embryo transfer and implantation.

Example 2

Analysis of Cohort Undergoing ART

An analysis was performed of a small cohort of women undergoing ART, hence during stimulated cycles. The collection of uterine lavage was performed during egg collection at hCG+2 (early secretory equivalent) in hormone stimulated cycles. Other ovulation triggers may be used such as GnRHa or another drug. Patients were subsequently classified as having 'pregnancy', 'no pregnancy', or pre-clinical pregnancy (i.e. despite an initial positive pregnancy test, no sac was detectable by ultrasound). In addition lavage from normally fertile women who were undergoing a hormone stimulated cycle as oocyte donors were also tested.

Figure 2A:
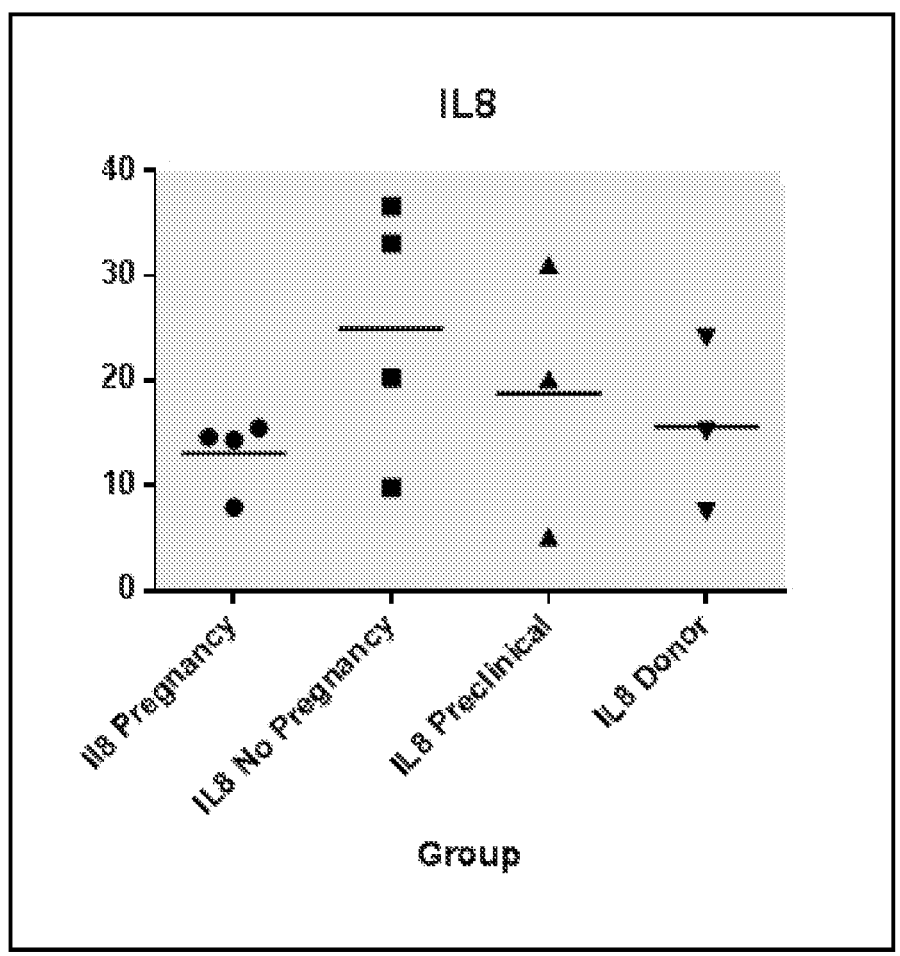
FIGS. 2A through C are a graphical representation of the levels of biomarkers in uterine lavage collected from women undergoing ART hormone stimulation cycles at hCG+2 (time of egg collection). Samples were analyzed for IL-8, G-CSF and VEGFA. Patients were defined by the outcome of the ART cycle, i.e. pregnancy, no pregnancy, preclinical pregnancy and fertile egg donor. Bars indicate mean values. Units are picogram/ml.
Figure 2B:
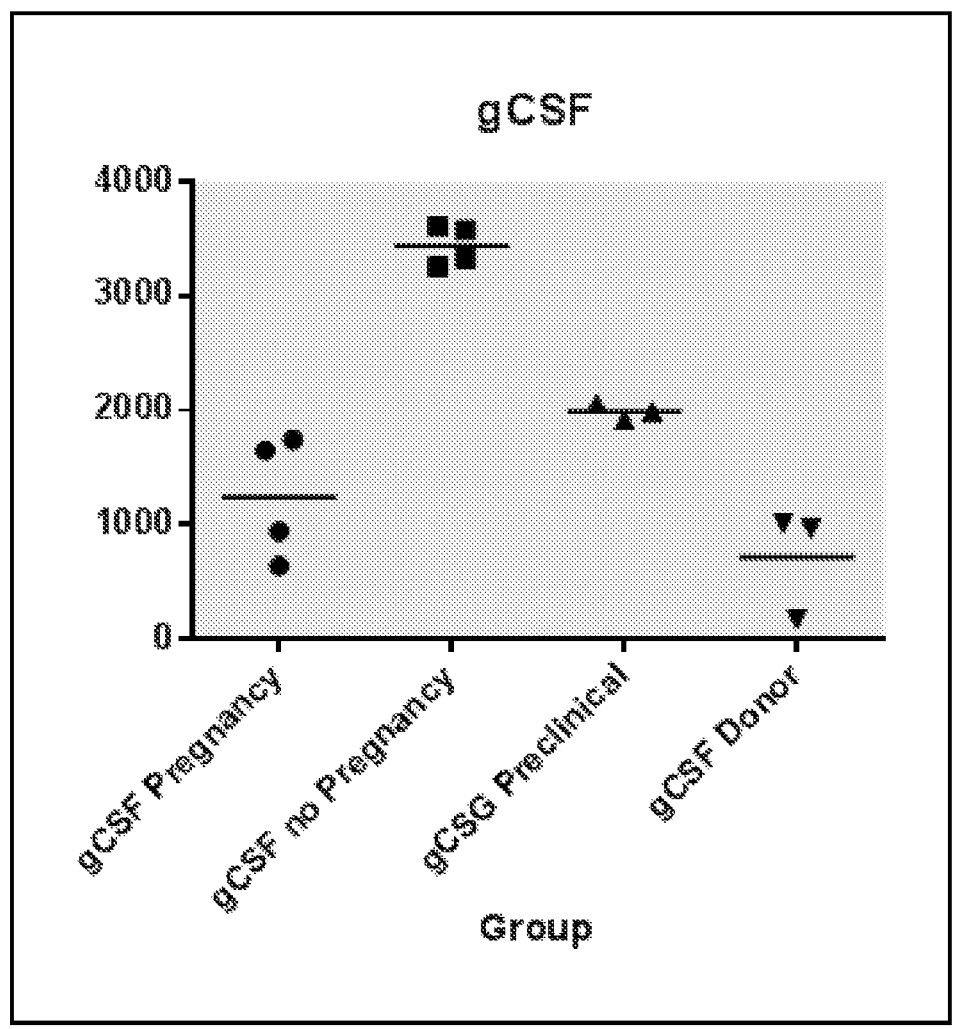
Figure 2C:
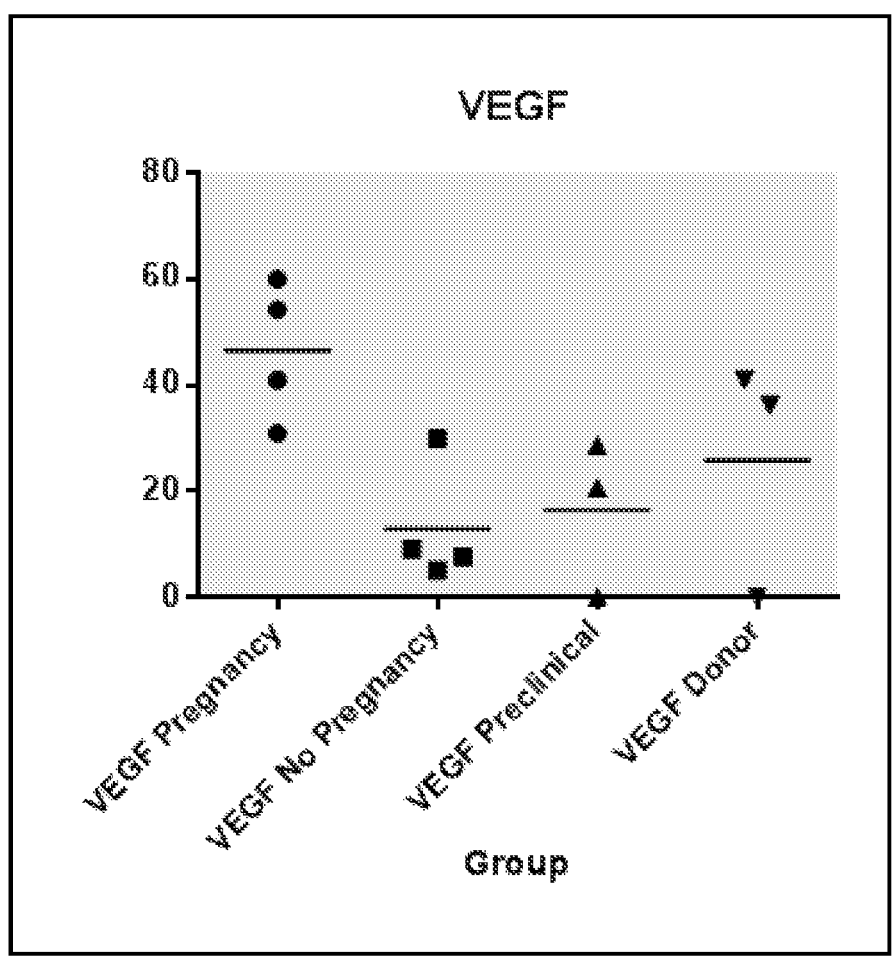

The results (FIG. 2) identified that G-CSF was significantly upregulated (p=0.0002) in women who did not become pregnant, compared with those that did. Additionally, it was seen that among the egg donors (otherwise fertile women) being stimulated that their level of G-CSF was similar to that of the infertile women for whom a pregnancy was attained. For women whose outcome was a preclinical pregnancy their G-CSF was to the higher end of the successful pregnancy group. This corresponds with the earlier data showing elevated G-CSF is indicative of an infertile endometrium.

VEGFA was reduced in women both unsuccessful and those who experienced a preclinical pregnancy. This may suggest that while G-CSF cannot discriminate pregnancy from preclinical pregnancy, VEGFA does potentially provide this discrimination.

IL-8 levels were elevated though not significantly in women who did not become pregnant compared to those who did. This is an apparent reversal of what was demonstrated in an initial study of natural cycles in which higher IL-8 levels were seen in the fertile cohort. Within the original study fertile group an elevated IL-8 is likely reflecting the beginning of receptivity and its associated inflammatory state. However, in these infertile women being stimulated with hormones, it is suggested that elevated IL-8 may reflect a chronically inflamed state of the endometrium. Hence, elevated IL-8 levels in treated infertile women may be detrimental and thus potentially useful in assessing response of women to hormone stimulation protocols.

Example 3

Assay

Data presented here identify a cohort of three biomarkers which are able to discriminate fertile and infertile women during the early secretory pre-receptive phase of their menstrual cycle. A subsequent study of a small number of women undergoing stimulated ART cycle revealed that individually G-CSF could discriminate those women who went on to become pregnant from those who did not. Additionally, VEGFA was able to discriminate clinical pregnancy from pre-clinical pregnancy, while IL-8 is elevated in women not becoming pregnant.

Example 4

Clinical Trial to Predict Outcome in Women Undergoing ART

Sample collection proceeded from women attending an IVF clinic for ART treatment. Samples collected were uterine lavage and serum; both being collected at the time of egg retrieval (OI+2 e.g. hCG+2 or GnRHa+2 or by another drug). Samples were collected from 122 women. It was elected to assay the samples and perform a t-test data analysis on all lavage and matched serum samples collected. Multivariate analysis of combined markers was performed using logitboost regression.

The dilution factor of the lavage was estimated using the formula: dilution factor=serum urea concentration divided by lavage urea concentration. Combining some lavage markers with some serum markers is also proposed.

Results

Total Number Participants=122.

Matched serum and lavage available=121.

Number of women with outcome of "pregnancy"=13 (three with later miscarriage).

Number of women with no embryo transfer performed (variety of reasons)=34 and excluded from this analysis as no outcome successful or otherwise can be determined.

Number of women with outcome of "no pregnancy"=72 BMI/Age available for 58 of these.

Number of women with outcome of "pre-clinical pregnancy"=2. These are excluded from analysis at present as it is unclear if there is any endometrial interaction with the embryo in a "preclinical" pregnancy.

Statistical analysis was performed by t-test to compare "no pregnancy" (n=72) with 'pregnancy' groups (n=13 included subsequent miscarriages). The inclusion of the subsequent miscarriages is questionable, as while some form of endometrial-embryo attachment has occurred it was not sufficient to maintain the pregnancy, thus whether the endometrium is "normal receptive" is unclear, however, it has been receptive to some level.

The earlier Examples tested lavage for combined G-CSF (CSF3), IL-8 and VEGFA. Additional factors CRP, IL-17, IL-6 and progesterone have also been included. Finally for this cohort, patient age and body mass index have been tested as part of the multivariate analysis.

Figure 3:
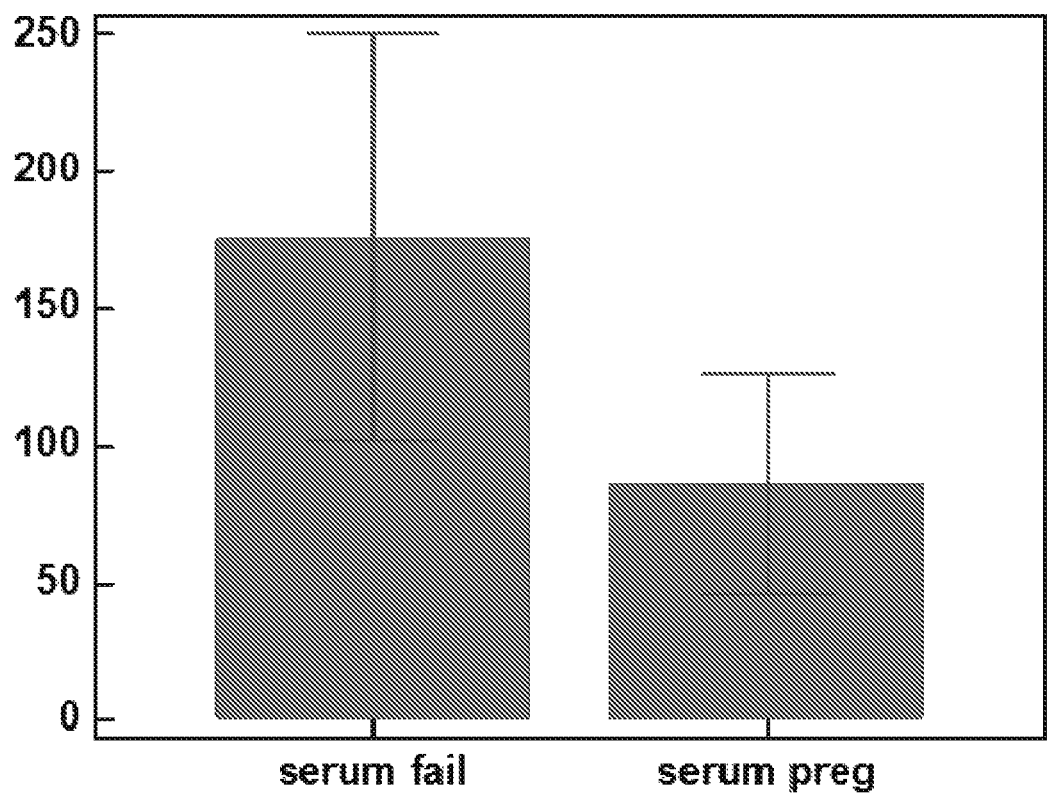
FIG. 3 is a graphical representation of G-CSF (CSF3) concentration in serum of women at hCG+2 (ovum collection). The participants are grouped according to ART cycle outcome of pregnancy (serum preg, n=13) and no pregnancy (serum fail, n=72).

Results are presented in Table 3 and FIG. 3.

TABLE 3

| | Biomarker levels | |
|---|---|---|
| Analyte | Lavage | Serum |
| G-CSF | P = 0.067 | P = 0.034 |
| IL-8 | P = 0.026 | P = 0.495 |
| VEGF | P = 0.154 | P = 0.463 |
| IL-6 | P = 0.451 | P = 0.075 |
| IL-17 | P = 0.005 | P = 0.261 |

Multivariate Analysis of Lavage

Biomarkers G-CSF, IL-8 and VEGFA combined with age and BMI give an ROC value of 0.969, p<0.0001. Criterion value of 0.573 gives 96.6% specificity, 84.6% sensitivity.

Multivariate Analysis of Serum

Pregnancy/miscarriage was compared with no pregnancy in the serum analysis.

Result 1: age, BMI, G-CSF, IL-8 and VEGFA (with patient physical attributes) produced a ROC area of 9.84, p<0.0001. Including only those who became pregnant and had no miscarriage. Criterion value of 0.741 gives 93.1% specificity, 100% sensitivity.

Result 2: age, BMI, G-CSF, IL-8 and VEGFA (with patient physical attributes) produced a ROC area of 0.981, p<0.0001. When including miscarriage women. Criterion value of 0.759 gives specificity 93.1%, sensitivity 100%.

Result 3: age, BMI, G-CSF, IL-8, VEGFA and progesterone produced a ROC area of 0.999, p<0.0001. When including miscarriage women. Criterion value of 0.699 gives 96.6% specificity at 100% sensitivity.

Result 4: age, BMI, G-CSF, IL-8, VEGFA and IL-6 produced a ROC area of 0.977, p<0.0001. When including miscarriage women. Criterion value of 0.657 gives 96.6% specificity, 84.6% sensitivity.

Result 5: age, BMI, G-CSF, IL-8, VEGFA and CRP produced a ROC area of 0.993, p<0.0001. When including miscarriage women. Criterion value of 0.481 with specificity 100% with 92.3% sensitivity.

Power analysis indicates serum IL-6 levels will achieve significance (p<0.05) with 360 samples. However, it is a combined analyte multivariate analysis using G-CSF together with supporting markers in lavage. Serum progesterone is proposed to provide a further analyte in the serum multivariate analysis.

The ability to use a serum based assay for endometrial receptivity has many advantages. Such an assay requires no invasive procedures of lavage or indeed biopsy/curettage collection.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Macaldowie et al. (2013) Assisted reproductive technology in Australia and New Zealand 2011, Sydney: National Perinatal Epidemiology and Statistics Unit, the University of New South Wales, Australia Sambrook et al, *Molecular Cloning, A Laboratory Manual.* (2nd ed.), 1989

The invention claimed is:

1. An assay for determining endometrial receptivity to implantation of an embryo in a female subject comprising
determining the concentrations of biomarkers of a fluid sample from the female subject wherein the biomarkers comprise IL-8, G-CSF and VEGFA, wherein the fluid sample is selected from the group consisting of uterine lavage, blood, plasma or serum, ascites, lymph fluid, tissue exudate or urine,
comparing the concentrations of the biomarkers to control values, and
determining an index of likelihood of endometrial receptivity or no receptivity, and
wherein the index indicates outcome as pregnancy when levels of IL-8 and/or G-CSF are reduced relative to the control;
wherein the index indicates outcome as no pregnancy when levels of IL-8 and/or G-CSF are elevated relative to the control;
wherein the index indicates outcome as pregnancy when level of VEGFA is elevated relative to the control; or
wherein the index indicates outcome as no pregnancy when level of VEGFA is reduced relative to the control.

2. The assay of claim 1 wherein one or more of a biomarker selected from CRP, IL-17, IL-6 and/or progesterone is also assayed.

3. The assay of claim 1 wherein the female subject is undergoing a hormone stimulated cycle.

4. The assay of claim 1 wherein the female subject is undergoing a natural ovulation cycle.

5. The assay of claim 1 wherein the fluid sample is a uterine lavage sample.

6. The assay of claim 1 wherein the fluid sample is a blood, plasma or serum sample.

7. The assay of claim 1 wherein the level of biomarkers is determined by an antibody-based assay.

8. An improved assisted reproductive technology protocol wherein the protocol comprises
sedating a female patient and harvesting eggs from the patient,
determining the level of IL-8, G-CSF and/or VEGFA in a uterine lavage, blood, plasma, serum, ascites, lymph fluid, tissue exudate or urine sample,
comparing the levels of IL-8, G-CSF and/or VEGFA to control values,
determining an index of likelihood of endometrial receptivity or no receptivity,
wherein the index indicates outcome as pregnancy when levels of IL-8 and/or G-CSF are elevated relative to control values and VEGFA is reduced relative to a control value and
wherein the index indicates outcome as no pregnancy when levels of IL-8 and/or G-CSF are reduced relative to control values and VEGFA is elevated relative to a control value, and whereby a decision of whether or not to proceed with implantation is made based on the index.

9. The improved assisted reproductive technology protocol of claim 8 wherein an elevated level of VEGFA is indicative of clinical pregnancy compared to a preclinical pregnancy whereas a reduced level of VEGFA is indicative of preclinical pregnancy compared to a clinical pregnancy.

10. The improved assisted reproductive technology protocol of claim 9 wherein an elevated level of G-CSF is an indication of a preclinical pregnancy and reduced level of G-CSF is an indication of clinical pregnancy.

11. The multiplex assay of claim 1 wherein the fluid sample is blood, plasma or serum.

12. The improved assisted reproduction technology protocol of claim 8 wherein the fluid sample is blood, plasma or serum.

13. The assay of claim 7 wherein the antibody-based assay comprises ECLIA, ELISA and Luminex LabMAP immunoassays.

* * * * *